United States Patent
Ouattara et al.

(10) Patent No.: US 11,458,077 B2
(45) Date of Patent: Oct. 4, 2022

(54) TWO-PHASE COSMETIC COMPOSITION COMPRISING A 4-(3-ALKOXY-4-HYDROXYPHENYL)ALKYL KETONE

(71) Applicant: L'OREAL, Paris (FR)

(72) Inventors: Sofiane Ouattara, Chevilly la Rue (FR); Véronique Chevalier, Chevilly la Rue (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/758,543

(22) PCT Filed: Oct. 18, 2018

(86) PCT No.: PCT/EP2018/078562
§ 371 (c)(1),
(2) Date: Apr. 23, 2020

(87) PCT Pub. No.: WO2019/081341
PCT Pub. Date: May 2, 2019

(65) Prior Publication Data
US 2020/0345593 A1    Nov. 5, 2020

(30) Foreign Application Priority Data
Oct. 25, 2017    (FR) ...................... 1760072

(51) Int. Cl.
| | | |
|---|---|---|
| *A61K 8/03* | (2006.01) | |
| *A61K 8/31* | (2006.01) | |
| *A61K 8/34* | (2006.01) | |
| *A61K 8/35* | (2006.01) | |
| *A61K 8/42* | (2006.01) | |
| *A61K 8/49* | (2006.01) | |
| *A61K 8/891* | (2006.01) | |
| *A61K 8/92* | (2006.01) | |
| *A61Q 5/02* | (2006.01) | |
| *A61Q 17/00* | (2006.01) | |

(52) U.S. Cl.
CPC ............... *A61K 8/03* (2013.01); *A61K 8/31* (2013.01); *A61K 8/345* (2013.01); *A61K 8/35* (2013.01); *A61K 8/42* (2013.01); *A61K 8/494* (2013.01); *A61K 8/891* (2013.01); *A61K 8/922* (2013.01); *A61Q 5/02* (2013.01); *A61Q 17/005* (2013.01); *A61K 2800/59* (2013.01)

(58) Field of Classification Search
CPC ........ A61Q 5/02; A61Q 17/005; A61K 8/345; A61K 8/35; A61K 8/494; A61K 8/42; A61K 8/03; A61K 8/891; A61K 8/31; A61K 8/922; A61K 2800/59
See application file for complete search history.

(56) References Cited

U.S. PATENT DOCUMENTS

| | | | |
|---|---|---|---|
| 2006/0015058 A1* | 1/2006 | Kellogg | A61B 5/14514 604/22 |
| 2009/0318853 A1* | 12/2009 | Reed | A61M 37/0092 604/22 |
| 2012/0251460 A1 | 10/2012 | Dalko | |
| 2014/0057991 A1* | 2/2014 | Chevalier | A61Q 5/00 514/678 |
| 2014/0249490 A1* | 9/2014 | Friedman | A61K 47/06 604/290 |
| 2017/0296445 A1* | 10/2017 | Skubsch | A61K 8/8152 |

FOREIGN PATENT DOCUMENTS

| | | |
|---|---|---|
| FR | 2 973 227 A1 | 10/2012 |
| JP | 2005-015401 A | 1/2005 |
| JP | 2006-343492 A | 12/2006 |
| JP | 2010-209116 A | 9/2010 |
| JP | 2014-509626 A | 4/2014 |
| WO | WO 03/069994 A1 | 8/2003 |
| WO | WO 2011/039445 A1 | 4/2011 |
| WO | WO 2012/130953 A1 | 10/2012 |
| WO | WO 2012/130954 A1 | 10/2012 |
| WO | WO-2012130953 A1 * | 10/2012 ............... A61K 8/39 |

* cited by examiner

*Primary Examiner* — Blessing M Fubara
(74) *Attorney, Agent, or Firm* — Polsinelli PC

(57) ABSTRACT

The invention relates to a composition comprising an aqueous phase and an oily phase which are visually separate and superimposed, 1,3-propanediol and a ketone compound of formula (I):

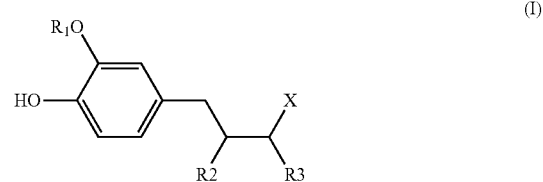

wherein R1 is a $C_2$-$C_4$ alkyl radical; R2 is H or a $C_1$-$C_4$ hydrocarbon-based radical; R3 is a $C_1$-$C_4$ hydrocarbon-based radical; and C—X is C=O.
The invention can be used for the cosmetic treatment of keratin materials.

21 Claims, No Drawings

TWO-PHASE COSMETIC COMPOSITION COMPRISING A 4-(3-ALKOXY-4-HYDROXYPHENYL)ALKYL KETONE

CROSS REFERENCE TO RELATED APPLICATIONS

This application is a National Phase filing under 35 U.S.C. § 371 of PCT/EP2018/078562 filed on 18 Oct. 2018; which application in turn claims priority to Application No. 1760072 filed in France on 25 Oct. 2017. The entire contents of each application are hereby incorporated by reference.

A subject of the present invention is a two-phase composition containing a compound of 4-(3-alkoxy-4-hydroxyphenyl)alkyl ketone type and 1,3-propanediol.

Compositions constituted of two distinct phases, in particular of a hydrophilic aqueous phase and of an oily phase, are generally denoted by the term "two-phase composition". They differ from emulsions in that, when at rest, the two phases are separate instead of being emulsified one in the other. Thus, the two phases are separated at rest by a single interface, whereas, in emulsions, one of the phases is dispersed in the other in the form of a multitude of droplets, and the interfaces are therefore multiple, these interfaces generally being stabilized with emulsifying surfactants and/or emulsifying polymers. The use of two-phase compositions requires prior agitation in order to form a homogeneous extemporaneous mixture. This mixture must be of sufficient quality and stability to enable homogeneous application of the two phases, but such that when at rest, the two phases become rapidly separated and regain their initial state, this phenomenon being more commonly known as "phase separation".

4-(3-Ethoxy-4-hydroxyphenyl)butan-2-one (ketone compound) is a beneficial substance as a preserving agent for cosmetic compositions, for protecting the compositions against microbial contamination, as described in application WO 2011/039445.

However, this ketone compound is has very low solubility in water or in glycerol: therefore its introduction into a two-phase composition causes a problem at the interface and the oily phase has an undesirable milky white appearance.

It therefore appears necessary to be able to use the ketone compound more easily in a two-phase composition. It is particularly sought to be able to have a two-phase composition having a well-defined interface, and also having good antimicrobial protection.

The inventors have discovered, unexpectedly, that the combination of 4-(3-ethoxy-4-hydroxyphenyl)butan-2-one with 1,3-propanediol makes it possible to obtain a satisfactory two-phase composition. The aqueous and oily phases of the composition are clear, without cloudy or milky appearance. The interface of the two-phase composition is well-defined, without exhibiting droplets, making the product attractive to consumers. The two-phase composition thus obtained has satisfactory and compliant antimicrobial protection.

More specifically, a subject of the invention is a composition comprising an aqueous phase and an oily phase which are visually distinct and superimposed, a ketone compound of formula (I) as defined below, and 1,3-propanediol.

A further subject of the invention is a process for the non-therapeutic cosmetic treatment of keratin materials, comprising the application to the keratin materials of a composition as described above. The process may be a cosmetic process for caring for or cleansing keratin materials.

The composition according to the invention comprises at least an aqueous phase and an oily phase which are visually distinct. These two phases are distinct, i.e. they are visible one on top of the other at rest and are separated by a single interface. The two phases may or may not be colored.

The duration of the phase separation may range from 3 to 30 minutes, better still from 5 to 25 minutes and preferably from 10 to 20 minutes.

Since the composition according to the invention is intended for topical application, it advantageously contains a physiologically acceptable medium, i.e. a medium that is compatible with the skin, mucous membranes, the hair and the scalp.

The composition according to the invention comprises a ketone compound of formula (I) below:

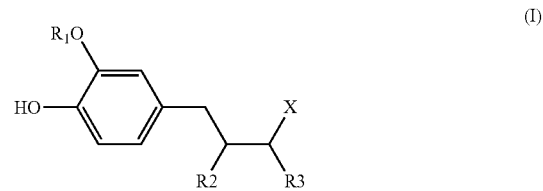

wherein:
R1 represents a $C_2$-$C_4$ alkyl radical,
R2 represents a hydrogen atom, or a saturated or unsaturated, linear or branched, $C_1$-$C_4$ hydrocarbon-based radical;
R3 represents a saturated or unsaturated, linear or branched, $C_1$-$C_4$ hydrocarbon-based radical optionally substituted with a hydroxyl group;
—C—X represents C=O.
Preferably, in formula (I):
R1 represents an ethyl radical;
R2 represents a hydrogen atom;
R3 represents a saturated or unsaturated, linear or branched, $C_1$-$C_4$ hydrocarbon-based radical optionally substituted with a hydroxyl group;
—C—X represents C=O.
Preferentially:
R1 represents an ethyl radical;
R2 represents a hydrogen atom;
R3 represents a saturated, linear $C_1$-$C_3$ hydrocarbon-based radical;
—C—X represents C=O.

As examples of compounds (I), mention may be made of:

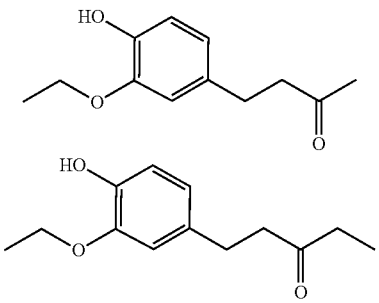

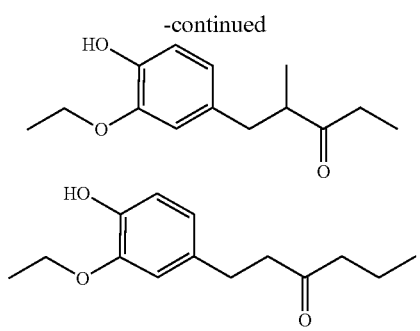

Preferably, the compound 4-(3-ethoxy-4-hydroxyphenyl) butan-2-one is used:

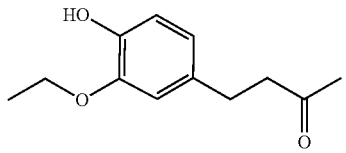

The compound (I) may be present in the composition according to the invention in a content ranging from 0.01% to 5% by weight, relative to the total weight of the composition, preferably ranging from 0.01% to 3% by weight, and preferentially ranging from 0.01 to 2.5% by weight.

The composition according to the invention comprises 1,3-propanediol which can be present in a content ranging from 0.1 to 50% by weight, relative to the total weight of the composition, preferably ranging from 1 to 20% by weight, and preferentially ranging from 2 to 10% by weight.

The composition according to the invention comprises an aqueous phase. Advantageously, the aqueous phase is present in a content ranging from 25% to 95% by weight, preferably from 30% to 90% by weight and preferentially from 50% to 80% by weight, relative to the total weight of the composition.

According to one embodiment, the composition according to the invention comprises from 20% to 95%, preferably from 25% to 90%, and preferentially from 45% to 80% by weight of water, relative to the total weight of the composition.

The composition may also comprise a polyol that is water-miscible at ambient temperature (25° C.), in particular chosen from polyols having in particular from 2 to 6 carbon atoms, such as glycerol, propylene glycol, butylene glycol, pentylene glycol and hexylene glycol. The water-miscible polyol may be present in the composition according to the invention in a content ranging from 0.1% to 40% by weight, preferably from 1% to 30% by weight, better still from 2 to 20% by weight and even better still from 2% to 10% by weight, relative to the total weight of the composition.

The composition according to the invention may comprise an electrolyte. The term "electrolyte" in the present invention is intended to mean all the salts and polyions, in particular polyanions, which can be used in a topical composition.

As an electrolyte which can be used in the composition according to the invention, mention may in particular be made of the salts of mono-, di- or trivalent metals, and more particularly the alkaline-earth metal salts, in particular the calcium salts, the alkali metal salts, for example the sodium and potassium salts, and also the magnesium, zinc, manganese and aluminum salts, and mixtures thereof.

The ions constituting these salts can be chosen, for example, from carbonates, bicarbonates, sulfates, phosphates, sulfonates, glycerophosphates, borates, bromides, chlorides, nitrates, acetates, hydroxides and persulfates.

Use may also be made of salts that are in the form of a solution or of a water containing them, and especially in the form of a spring or mineral water. In general, a mineral water is fit for consumption, which is not always the case for a spring water. Each of these waters contains, inter alia, dissolved minerals and trace elements.

The spring water or mineral water used may be chosen, for example, from Vittel water, Vichy basin water, Uriage water, Roche-Posay water, Bourboule water, Enghien-les-Bains water, Saint Gervais-les-Bains water, Néris-les-Bains water, Allevard-les-Bains water, Digne water, Maizières water, Neyrac-les-Bains water, Lons-le-Saunier water, Eaux Bonnes water, Rochefort water, Saint Christau water, Fumades water, Avène water and Tercis-les-Bains water.

Advantageously, the electrolyte is chosen from sodium chloride, potassium chloride and magnesium chloride.

The electrolyte may be present in the composition in a content ranging from 0.05 to 5% by weight, preferably from 0.1 to 3% by weight, and preferentially ranging from 0.15 to 2% by weight, relative to the total weight of the composition.

According to one particular embodiment of the invention, the weight ratio between the aqueous phase and the oily phase ranges from 10/90 to 90/10, preferably from 25/75 to 90/10, even more preferentially from 30/70 to 80/20 and better still from 40/60 to 70/30.

The oily phase generally represents from 3 to 74% by weight, preferably from 8 to 68% by weight, more preferentially from 13 to 48% by weight relative to the total weight of the composition.

The oily phase of the composition according to the invention may comprise one or more oils, these oils possibly being chosen from hydrocarbon-based, mineral, plant and synthetic oils, or alternatively silicone oils. It may also comprise liposoluble or lipodispersible additives.

The term "hydrocarbon-based oil" is intended to mean an oil formed essentially from, or even constituted of, carbon and hydrogen atoms, and possibly oxygen and nitrogen atoms, and containing no silicon or fluorine atoms; it may contain ester, ether, amine or amide groups.

As hydrocarbon-based oils that may be used in the composition of the invention, examples that may be mentioned include:

synthetic esters and ethers, especially of fatty acids, for instance the oils of formulae $R^1COOR^2$ and $R^1OR^2$ wherein $R^1$ represents a fatty acid residue containing from 8 to 29 carbon atoms and $R^2$ represents a branched or unbranched hydrocarbon-based chain containing from 3 to 30 carbon atoms; for instance purcellin oil, isononyl isononanoate, isopropyl myristate, isopropyl palmitate, 2-ethylhexyl palmitate, 2-octyldodecyl stearate, 2-octyldodecyl erucate or isostearyl isostearate; hydroxylated esters, for instance isostearyl lactate, octyl hydroxystearate, octyldodecyl hydroxystearate, diisostearyl malate, triisocetyl citrate, and fatty alkyl heptanoates, octanoates and decanoates; polyol esters, for instance propylene glycol dioctanoate, neopentyl glycol diheptanoate and diethylene glycol diisononanoate; and pentaerythritol esters, for instance pentaerythrityl tetraisostearate;

hydrocarbon-based oils of plant origin, such as perhydrosqualene, liquid triglycerides of fatty acids containing from 4 to 10 carbon atoms, for instance heptanoic or octanoic acid triglycerides, or alternatively, for example, sunflower oil, maize oil, soybean oil, marrow oil, grapeseed oil, sesame seed oil, hazelnut oil, apricot kernel oil, macadamia oil, arara oil, coriander oil, castor oil, avocado oil, caprylic/capric acid triglycerides, jojoba oil, shea butter oil, meadowfoam oil and argan oil;

volatile or nonvolatile, linear or branched hydrocarbons, of mineral or synthetic origin, and derivatives thereof, such as liquid petroleum jelly and hydrogenated polyisobutene such as Parleam® oil; $C_8$-$C_{16}$ branched alkanes or isoalkanes (also known as isoparaffins), isododecane, isodecane, isohexadecane, for instance the isoparaffins sold under the trade name Isopar by the company Exxon Chemical or the oils sold under the trade name Permethyl by the company Presperse; and mixtures thereof;

linear alkanes, especially of plant origin, preferably comprising from 7 to 14 carbon atoms;

fatty alcohols that are liquid at ambient temperature, containing from 8 to 26 carbon atoms, for instance octyldodecanol, 2-butyloctanol, 2-hexyldecanol, 2-undecylpentadecanol or oleyl alcohol.

The term "silicone oil" is intended to mean an oil containing at least one silicon atom, and in particular containing Si—O groups.

The silicone oil(s) may be volatile or nonvolatile.

The term "volatile" refers to a compound that can evaporate on contact with the skin in less than one hour, at ambient temperature and atmospheric pressure. The volatile oil is a volatile cosmetic oil, which is liquid at ambient temperature, especially having a non-zero vapor pressure, at ambient temperature and atmospheric pressure, in particular having a vapor pressure ranging from 0.13 Pa to 40 000 Pa ($10^{-3}$ to 300 mmHg), preferably ranging from 1.3 Pa to 13 000 Pa (0.01 to 100 mmHg) and preferentially ranging from 1.3 Pa to 1300 Pa (0.01 to 10 mmHg).

Examples of volatile silicone oils that may be mentioned include cyclopolydimethylsiloxanes (INCI name: cyclomethicone), such as cyclopentasiloxane, cyclohexasiloxane, octamethylcyclotetrasiloxane, decamethylcyclopentasiloxane, dodecamethylcyclohexasiloxane; linear silicones such as heptamethylhexyltrisiloxane, heptamethyloctyltrisiloxane, hexamethyldisiloxane, octamethyltrisiloxane, decamethyltetrasiloxane and dodecamethylpentasiloxane.

Preferably, the volatile silicone oil is chosen from cyclopentasiloxane and cyclohexasiloxane.

Nonvolatile silicone oils that may be mentioned include silicone oils such as polymethylsiloxanes, especially PDMS, and phenyl polymethylsiloxanes such as phenyl trimethicones, phenyl dimethicones, phenyltrimethylsiloxydiphenylsiloxanes, diphenyl dimethicones, diphenylmethyldiphenyltrisiloxanes, 2-phenylethyltrimethyl siloxysilicates and polymethylphenylsiloxanes; polysiloxanes modified with fatty acids, fatty alcohols or polyoxyalkylenes, and mixtures thereof.

According to a particular embodiment of the invention, the oil(s) are chosen from hydrocarbon-based oils. According to a preferential embodiment, the oil(s) are chosen from fatty acid esters such as isopropyl palmitate and isononyl isononanoate, fatty alcohol ethers, plant oils, mineral oils such as liquid petroleum jelly, fatty alcohols that are liquid at ambient temperature and liquid fatty acid triglycerides. Preferably, the oil(s) are chosen from fatty acid esters such as isononyl isononanoate, plant oils and liquid fatty acid triglycerides. The oils may optionally be constituted solely of volatile oils.

Advantageously, the oily phase is above the aqueous phase when the composition according to the invention is at rest.

The two-phase composition according to the invention may optionally comprise one or more surfactants in either of the phases, in particular when it is used as a makeup removal or cleansing composition, since the presence of a surfactant makes it possible at the same time to obtain good makeup removal of the makeup compositions. However, the composition of the invention may also be free of surfactant, and, if it contains any, the amount of surfactant should be such that the composition remains at rest in the form of two separate phases and not in the form of an emulsion.

Advantageously, the composition according to the invention can comprise a nonionic surfactant, preferably nonsilicone surfactant.

The nonionic surfactant may be chosen from:
$C_8$-$C_{30}$ fatty alcohol ethers of a sugar, in particular ($C_8$-$C_{30}$) alkyl (poly)glucosides,
ethers of polyethylene glycol, in particular containing from 15 to 25 ethylene oxide units, and of a $C_8$-$C_{30}$ fatty acid ester of glucose or of methylglucose,
$C_8$-$C_{30}$ fatty acid esters of sorbitan,
polyoxyethylenated $C_8$-$C_{30}$ fatty acid esters of sorbitan, especially containing from 2 to 20 mol of ethylene oxide,
polyoxyethylenated $C_8$-$C_{30}$ fatty acid esters of sorbitan, especially containing from 2 to 20 mol of ethylene oxide,
$C_8$-$C_{30}$ fatty acid monoesters or diesters of glycerol,
polyglycerolated $C_8$-$C_{30}$ fatty acid esters, especially containing from 2 to 16 mol of glycerol,
$C_8$-$C_{30}$ fatty acid esters of polyethylene glycol, especially containing from 2 to 20 ethylene oxide units,
$C_8$-$C_{30}$ fatty acid esters of glucose or of ($C_1$-$C_2$)alkylglucose or of sucrose,
and mixtures thereof;

Preferably, the nonionic surfactant can be chosen from ($C_8$-$C_{30}$)alkyl (poly)glucosides.

The nonionic surfactants may also be chosen from $C_8$-$C_{30}$ fatty alcohol ethers of a sugar, in particular ($C_8$-$C_{30}$)alkyl (poly)glucosides.

The alkyl (poly)glucoside may be chosen from a group comprising the compounds having the following general formula:

$$R_1O\text{-}(G)_a$$

wherein $R_1$ denotes a linear or branched alkyl radical comprising from 8 to 30 carbon atoms and preferably from 8 to 24 carbon atoms, the G group denotes a sugar comprising from 5 to 6 carbon atoms and a is a number ranging from 1 to 10, and mixtures thereof.

The alkyl (poly)glucoside may be chosen especially from the group comprising $C_8$-$C_{22}$ fatty alcohol ethers or mixtures of ethers of glucose or of xylose, preferably of glucose.

The unit (or chain) derived from the fatty alcohol of the ethers may be chosen especially from caprylyl, capryl, decyl, lauryl, myristyl, cetyl (or palmityl), stearyl, octyldodecyl, arachidyl, behenyl and hexadecanoyl units, and mixtures thereof such as cetearyl.

In a particular embodiment, the alkyl (poly)glucoside is chosen from caprylyl/capryl glucoside, decyl glucoside, lauryl glucoside, myristyl glucoside, cetearyl glucoside, arachidyl glucoside, cocoyl glucoside, octyldodecyl glucoside, caprylyl/capryl xyloside, octyldodecyl xyloside, and a mixture thereof, preferably cetearyl glucoside and arachidyl glucoside.

Examples of alkyl (poly)glucosides that may be mentioned include caprylyl/capryl glucoside, for instance the product sold under the name Oramix CG 110 by the company SEPPIC, decyl glucoside sold, for example, under the names Plantaren 2000 by the company Henkel, Plantacare 2000 UP by the company Cognis, Mydol 10 by the company Kao, or Oramix NS 10 by the company SEPPIC, lauryl glucoside sold, for example, by the company Henkel under the name Plantaren 1200, coco glucoside sold, for example, under the name Plantacare 818 UP by the company Cognis, cetearyl glucoside optionally as a mixture with cetearyl alcohol, sold, for example, under the name Montanov 68 by the company SEPPIC or under the name Xyliance by the company Soliance, under the name Tego Care CG90 by the company Evonik Goldschmidt and under the name Emulgade KE 3302 by the company Henkel, and also arachidyl glucoside, for example in the form of the mixture of arachidyl and behenyl alcohols and of arachidyl glucoside, sold under the name Montanov 202 by the company SEPPIC, the mixture of cocoyl polyglucoside and of cetyl and stearyl alcohols (35/65) sold, for example, under the name Montanov 82 by the company SEPPIC, octyldodecyl xyloside sold under the names Fluidanov 20X or Easynov by the company SEPPIC, myristyl glucoside, and especially in the form of a mixture with myristyl alcohol, for instance the product sold by the company SEPPIC under the name Montanov 14, mixtures of (C12-C20)alkyl glucosides especially as a mixture with C14 to C22 fatty alcohols, for instance the mixture sold under the name Montanov L by the company SEPPIC, and mixtures thereof.

The ethers of polyethylene glycol, especially containing from 15 to 25 ethylene oxide units, and of a C8-C30 fatty acid ester of glucose or of methylglucose, may be chosen from: the ether of polyethylene glycol containing about 20 mol of ethylene oxide and of the mixture of methylglucose monoester and diester of caprylic/capric acids (INCI name: PEG-20 methyl glucose sesquicaprylate/sesquicaprate)

the ether of polyethylene glycol containing about 20 mol of ethylene oxide and of the mixture of methylglucose monoester and diester of lauric acid (INCI name: PEG-20 methyl glucose sesquilaurate)

the ether of polyethylene glycol containing about 20 mol of ethylene oxide and of the mixture of methylglucose monoester and diester of stearic acid (INCI name: PEG-20 methyl glucose sesquistearate)

the ether of polyethylene glycol containing about 20 mol of ethylene oxide and of the methylglucose diester of stearic acid (INCI name: PEG-20 methyl glucose distearate)

The $C_8$-$C_{30}$ and preferably $C_{12}$-$C_{22}$ fatty acid esters (especially monoesters, diesters and triesters) of sorbitan may be chosen from:

sorbitan caprylate; sorbitan cocoate; sorbitan isostearate; sorbitan laurate; sorbitan oleate;

sorbitan palmitate; sorbitan stearate sorbitan diisostearate; sorbitan dioleate; sorbitan distearate;

sorbitan sesquicaprylate; sorbitan sesquiisostearate; sorbitan sesquioleate; sorbitan sesquistearate;

sorbitan triisostearate; sorbitan trioleate; sorbitan tristearate;

The polyoxyethylenated $C_8$-$C_{30}$ (preferably $C_{12}$-$C_{18}$) fatty acid esters (especially monoesters, diesters and triesters) of sorbitan especially containing from 2 to 20 mol of ethylene oxide may be chosen from polyoxyethylenated esters of $C_{12}$-$C_{18}$ fatty acids, in particular lauric, myristic, cetylic or stearic acid, of sorbitan especially containing from 2 to 30 mol of ethylene oxide, such as:

polyoxyethylenated sorbitan monolaurate (4 OE) (Polysorbate-21)

polyoxyethylenated sorbitan monolaurate (20 OE) (Polysorbate-20)

polyoxyethylenated sorbitan monopalmitate (20 OE) (Polysorbate-40)

polyoxyethylenated sorbitan monostearate (20 OE) (Polysorbate-60)

polyoxyethylenated sorbitan monostearate (4 OE) (Polysorbate-61)

polyoxyethylenated sorbitan monooleate (20 OE) (Polysorbate-80)

polyoxyethylenated sorbitan monooleate (5 OE) (Polysorbate-81)

polyoxyethylenated sorbitan tristearate (20 OE) (Polysorbate-65)

polyoxyethylenated sorbitan trioleate (20 OE) (Polysorbate-85)

The polyoxyethylenated $C_8$-$C_{30}$ (preferably $C_{12}$-$C_{18}$) fatty acid esters (especially monoesters, diesters, triesters and tetraesters) of sorbitan, especially containing from 2 to 20 mol of ethylene oxide, may be chosen from polyoxyethylenated esters, especially containing from 2 to 20 mol of ethylene oxide, of $C_{12}$-$C_{18}$ fatty acids, in particular such as lauric, myristic, cetylic or stearic acid, and of sorbitan, such as:

the ester polyoxyethylenated with 20 OE of sorbitan and of cocoic acid (PEG-20 sorbitan cocoate)

The polyoxyethylenated esters (especially containing from 2 to 20 OE) of sorbitan and of isostearic acid (such as PEG-2 sorbitan isostearate; PEG-5 sorbitan isostearate; PEG-20 sorbitan isostearate such as the product sold under the name Nikkol TI 10 V by the company Nikkol)

The polyoxyethylenated esters (especially containing from 2 to 20 OE) of sorbitan and of lauric acid (such as PEG-10 sorbitan laurate)

The polyoxyethylenated esters (especially containing from 2 to 20 OE) of sorbitan and of oleic acid containing 10 oxyethylene groups (such as PEG-6 sorbitan oleate; PEG-20 sorbitan oleate)

The polyoxyethylenated esters (in particular containing from 3 to 20 OE) of sorbitan and of stearic acid (such as PEG-3 sorbitan stearate; PEG-4 sorbitan stearate; PEG-6 sorbitan stearate);

The $C_8$-$C_{30}$ (preferably $C_{12}$-$C_{18}$) fatty acid monoesters of glycerol may be chosen from glyceryl caprylate, glyceryl caprate, glyceryl laurate, glyceryl myristate, glyceryl palmitate, glyceryl isostearate (Peceol Isostéarique from Gattefossé), glyceryl stearate, glyceryl oleate, glyceryl cocoate, glyceryl behenate (Compritol 888 ATO from Gattefossé), glyceryl arachidate;

The glycerol diesters such as glyceryl dilaurate, glyceryl dimyristate, glyceryl dipalmitate, glyceryl diisostearate, glyceryl distearate, glyceryl dioleate, glyceryl dibehenate, glyceryl diarachidate, The polyglycerolated $C_8$-$C_{30}$ fatty acid esters especially containing from 2 to 16 mol of glycerol may be chosen from polyglycerolated esters of $C_{12}$-$C_{18}$ fatty acids, in particular lauric, myristic, palmitic, stearic or isostearic acid, especially containing from 2 to 16 mol of glycerol, such as:

polyglyceryl-2 laurate, polyglyceryl-3 laurate, polyglyceryl-4 laurate, polyglyceryl-5 laurate, polyglyceryl-6 laurate, polyglyceryl-10 laurate;

polyglyceryl-2 myristate, polyglyceryl-3 myristate, polyglyceryl-4 myristate, polyglyceryl-5 myristate, polyglyceryl-6 myristate, polyglyceryl-10 myristate;

polyglyceryl-2 palmitate, polyglyceryl-3 palmitate, polyglyceryl-6 palmitate, polyglyceryl-10 palmitate;

polyglyceryl-2 isostearate, polyglyceryl-3 isostearate, polyglyceryl-4 isostearate, polyglyceryl-5 isostearate, polyglyceryl-6 isostearate, polyglyceryl-10 isostearate;

polyglyceryl-2 stearate, polyglyceryl-3 stearate, polyglyceryl-4 stearate, polyglyceryl-5 stearate, polyglyceryl-6 stearate, polyglyceryl-8 stearate, polyglyceryl-10 stearate.

The $C_8$-$C_{30}$ (preferably $C_{12}$-$C_{18}$) fatty acid esters of polyethylene glycol, especially containing from 2 to 20 ethylene oxide units, may be chosen from:

PEG-8 behenate; PEG-8 caprylate; PEG-8 caprate; PEG-6 caprylate/caprate; PEG-8 caprylate/caprate; PEG-5 cocoate; PEG-8 cocoate; PEG-9 cocoate; PEG-10 cocoate;

PEG-15 cocoate; PEG-4 ethylhexanoate; PEG-5 ethylhexanoate; PEG-13 ethylhexanoate;

PEG-2 isostearate; PEG-4 isostearate; PEG-6 isostearate; PEG-8 isostearate; PEG-10 isostearate; PEG-12 isostearate; PEG-20 isostearate; PEG-2 laurate; PEG-4 laurate; PEG-6 laurate; PEG-8 laurate; PEG-9 laurate; PEG-10 laurate; PEG-12 laurate; PEG-14 laurate;

PEG-20 laurate; PEG-2 oleate; PEG-4 oleate; PEG-6 oleate; PEG-8 oleate; PEG-10 oleate;

PEG-12 oleate; PEG-14 oleate; PEG-16 oleate; PEG-20 oleate; PEG-6 palmitate; PEG-18 palmitate; PEG-20 palmitate; PEG-2 stearate; PEG-4 stearate; PEG-6 stearate; PEG-8 stearate; PEG-10 stearate; PEG-14 stearate; PEG-18 stearate; PEG-20 stearate.

The $C_8$-$C_{30}$ (preferably $C_{12}$-$C_{18}$) fatty acid esters of glucose or of ($C_1$-$C_2$)alkylglucose or of sucrose may be chosen from glucose palmitate, ($C_1$-$C_2$)alkylglucose sesquistearates, for instance methylglucose sesquistearate, ($C_1$-$C_2$)alkylglucose palmitates, for instance methylglucose palmitate or ethylglucose palmitate, fatty esters of methylglucoside and more especially the diester of methylglucose and of oleic acid (INCI name: Methyl glucose dioleate); the ester of methylglucose and of isostearic acid (INCI name: Methyl glucose isostearate); the ester of methylglucose and of lauric acid (INCI name: Methyl glucose laurate); the mixture of the monoester and diester of methylglucose and of isostearic acid (INCI name: methyl glucose sesquiisostearate); the mixture of the monoester and diester of methylglucose and of stearic acid (INCI name: methyl glucose sesquistearate) and in particular the product sold under the name Glucate SS by the company Amerchol, and mixtures thereof.

Sucrose esters that may be mentioned include sucrose cocoate; sucrose dilaurate; sucrose distearate; sucrose laurate; sucrose myristate; sucrose oleate; sucrose palmitate and sucrose stearate.

The nonionic surfactant may be present in the composition according to the invention in a content ranging from 0.1 to 5% by weight, preferably from 0.1 to 3% by weight, even better still from 0.1 to 1% by weight and even better still ranging from 0.1 to 0.5% by weight, relative to the total weight of the composition.

The nonionic surfactant is in particular present in an amount such that the two aqueous and oily phases remain distinct at rest and do not mix to form an emulsion.

Advantageously, the composition according to the invention can comprise a niacinamide compound.

The niacinamide compound can be chosen from niacinamide (also known as vitamin B3), N,N-diethylniacinamide, N-picolylniacinamide and N-allylniacinamide. According to one preferred embodiment, the niacinamide compound is niacinamide.

The niacinamide compound can be present in the composition according to the invention in a content ranging from 0.01 to 10% by weight, preferably from 0.05 to 5% by weight, and even better still from 0.2 to 3% by weight, relative to the total weight of the composition.

Advantageously, the composition according to the invention can comprise a xanthine compound of formula (II) below:

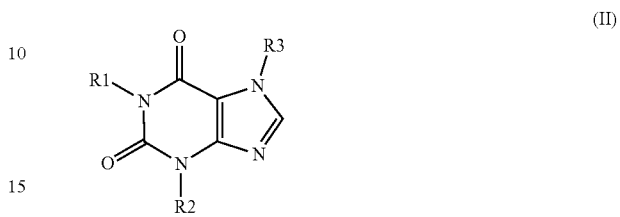

wherein:

R1, R2 and R3, independently of one another, denote a hydrogen atom or a methyl or ethyl radical, preferably a hydrogen atom or a methyl radical, and more preferentially a methyl radical.

The compound (I) may be xanthine (R1=R2=R3=H), caffeine (R1=R2=R3=methyl), theobromine (R1=H; R2=R3=methyl), theophylline (R1=R2=methyl; R3=H) and paraxanthine (R1=R3=methyl; R2=H).

Advantageously, the xanthine compound (II) is caffeine.

The composition may comprise a mixture of the niacinamide compounds and the xanthine compounds described above.

The xanthine compound (II) can be present in the composition according to the invention in a content ranging from 0.01 to 10% by weight, preferably from 0.05 to 5% by weight, and even better still from 0.2 to 3% by weight, relative to the total weight of the composition.

The niacinamide compound and/or the xanthine compound make(s) it possible in particular to obtain a two-phase composition having a perfectly well-defined interface at rest.

The composition according to the invention may also contain conventional cosmetic adjuvants or additives, which will be in one or other phase depending on their hydrophilic or lipophilic nature, for instance fragrances, preserving agents, dyes, humectants, UV-screening agents (or sunscreens), pH adjusters, gelling agents, and mixtures thereof.

The composition according to the invention may be used for any topical application; it may especially constitute a cosmetic or dermatological composition. It may in particular be used for caring for, cleansing and/or removing makeup from the skin, the lips and/or the eyes, and also as a haircare composition.

According to a preferred embodiment of the invention, the composition is a composition for caring for bodily and/or facial skin.

Another subject of the invention is a process for preparing a composition, in particular a cosmetic or dermatological composition, comprising:

a step of preparing the aqueous phase by mixing the ingredients constituting the aqueous phase, in particular the ketone compound (I) and the 1,3-propanediol;

a step of preparing the oily phase by mixing the constituents of the oily phase;

then a step of mixing the aqueous phase and the oily phase, said steps possibly being carried out at a temperature ranging from 20 to 40° C.

The invention is illustrated in greater detail in the examples that follow. The contents of the ingredients are expressed as weight percentages.

COMPARATIVE EXAMPLES 1 TO 9

The following 4 two-phase compositions according to the invention (examples 1 to 4) and 5 compositions outside the invention (examples 5 to 9) were prepared (contents by weight percentage) and the appearance of each composition obtained was observed.

The challenge-test method is constituted of an artificial contamination of the sample with microbial strains from a collection (bacteria, yeasts and moulds) and of an evaluation of the number of revivable microorganisms seven days after inoculation.

In order to demonstrate the effect of the composition tested, the antimicrobial activity of the composition tested

|  | Example 1 | Example 2 | Example 3 | Example 4 |
|---|---|---|---|---|
| Polydimethylsiloxane 10 cSt | 9 | 9 | 9 | 9 |
| Isohexadecane | 6 | 6 | 6 | 6 |
| Decyl glucoside in aqueous solution at 55% by weight (ORAMIX NS 10 from SEPPIC) | 0.17 | 0.17 | 0.17 | 0.17 |
| Hexylene glycol | 0.4 | 0.4 | 0.4 | 0.4 |
| Sodium chloride | 0.4 | 0.4 | 0.4 | 0.4 |
| Potassium phosphate | 1 | 1 | 1 | 1 |
| Sequestrant | 0.2 | 0.2 | 0.2 | 0.2 |
| 4-(3-ethoxy-4-hydroxyphenyl)butan-2-one | 0.5 | 0.5 | 0.5 | 0.5 |
| 1,3-propanediol | 5 | 5 | 5 | 5 |
| niacinamide | — | 3 | — | 3 |
| caffeine | — | — | 1 | 1 |
| Water | qs 100 | qs 100 | qs 100 | qs 100 |
| Appearance at T0 | Two-phase with 2 clear and colorless phases | Two-phase with 2 clear and colorless phases | Two-phase with 2 clear and colorless phases | Two-phase with 2 clear and colorless phases |

|  | Example 5* Placebo | Example 6* | Example 7* | Example 8* | Example 9* |
|---|---|---|---|---|---|
| Polydimthylsiloxane 10 cSt | 9 | 9 | 9 | 9 | 9 |
| Isohexadecane | 6 | 6 | 6 | 6 | 6 |
| Decyl glucoside in aqueous solution at 55% by weight (ORAMIX NS 10 from SEPPIC) | 0.17 | 0.17 | 0.17 | 0.17 | 0.17 |
| Hexylene glycol | 0.4 | 0.4 | 0.4 | 0.4 | 0.4 |
| Sodium chloride | 0.4 | 0.4 | 0.4 | 0.4 | 0.4 |
| Potassium phosphate | 1 | 1 | 1 | 1 | 1 |
| Sequestrant | 0.2 | 0.2 | 0.2 | 0.2 | 0.2 |
| 4-(3-ethoxy-4-hydroxyphenyl)butan-2-one | — | 0.5 | — | — | — |
| 1,3-propanediol | — | — | 5 | — | — |
| niacinamide | — | — | — | 3 | — |
| caffeine | — | — | — | — | 1 |
| Water | qs 100 | qs 100 | qs 100 | qs 100 | qs 100 |
| Appearance at T0 | Two-phase with white oily phase | Two-phase with white oily phase | Two-phase with white oily phase | Two-phase with white oily phase | Two-phase with white oily phase |

The antimicrobial protection of each two-phase composition of examples 1 to 4 according to the invention was also evaluated according to the following protocol:

was compared with the same solution alone (control), after inoculation of approximately $10^6$ CFU (Colony Forming Units)/gram of aqueous solution.

Microorganism Cultures
5 pure cultures of microorganisms are used.

| MICROORGANISMS | Subculturing medium | T° | ATCC |
|---|---|---|---|
| *Escherichia coli* (Ec) | Trypto-casein soya | 35° C. | 8739 |
| *Enterococcus faecalis* (Ef) | Trypto-casein soya | 35° C. | 33186 |
| *Pseudomonas aeruginosa* (Pa) | Trypto-casein soya | 35° C. | 19429 |
| *Candida albicans* (Ca) | Sabouraud | 35° C. | 10231 |
| *Aspergillus niger* (An) | Malt | 35° C. | 6275 |

ATCC = American Type Culture Collection

The strains of gram-negative bacteria (*Escherichia coli* and *Pseudomonas aeruginosa*), gram-positive bacterium (*Enterococcus faecalis*), yeast (*Candida albicans*), and mould (*Aspergillus niger*) are inoculated into subculturing medium, respectively the day before inoculation for the bacteria and the yeast, and 5 days before inoculation for the mould.

On the day of inoculation:
a suspension in tryptone salt diluent is prepared, respectively, for the bacteria and the yeast, so as to obtain by spectrophotometer a suspension with an optical density of between 35% and 45% of transmitted light at 544 nm;
for the mould, the spores are collected by washing the agar with 6 to 7 ml of harvesting solution and the suspension is recovered in a sterile tube or flask.

After homogenizing the microbial suspension, 0.2 ml of microbial suspension is introduced into each pill bottle (the suspensions are used pure: between $1 \times 10^8$ and $3 \times 10^8$ CFU per ml) and the microbial suspension is thoroughly homogenized in the 20 g of composition to be tested, using a spatula.

The content of microorganisms present in the product corresponds after homogenization to a concentration of $10^6$ microorganisms per gram of product, i.e. inoculation at 1% of an inoculum containing $10^8$ microorganisms per ml.

After 7 days of contact time between the microorganisms and the product at 22° C.±2° C. and in the dark, ten-fold dilutions are performed and the number of revivable microorganisms remaining in the product is counted. The results are expressed in log.

The following results were obtained:

| | E. coli | P. aeruginosa | E. faecalis | C. albicans | A. niger | Result |
|---|---|---|---|---|---|---|
| Ex 1 | −4 | −4 | −4 | −4 | −4 | compliant |
| Ex 2 | −4 | −4 | −4 | −4 | −4 | compliant |
| Ex 3 | −4 | −4 | −4 | −4 | −4 | compliant |
| Ex 4 | −4 | −4 | −4 | −4 | −4 | compliant |

The two-phase compositions according to the invention (examples 1 to 4) exhibit conforming antimicrobial protection.

COMPARATIVE EXAMPLES 10 TO 12

The following 2 two-phase compositions according to the invention (examples 10 to 11) and a composition outside the invention (example 12) were prepared (contents by weight percentage) and the appearance of each composition obtained was observed.

| | Example 10 | Example 11 | Example 12* |
|---|---|---|---|
| cyclopentasiloxane | 9 | 9 | 9 |
| Isohexadecane | 6 | 6 | 6 |
| Decyl glucoside in aqueous solution at 55% by weight (ORAMIX NS 10 from SEPPIC) | 0.17 | 0.17 | 0.17 |
| Hexylene glycol | 0.4 | 0.4 | 0.4 |
| Sodium chloride | 0.4 | 0.4 | 0.4 |
| Potassium phosphate | 1 | 1 | 1 |
| Sequestrant | 0.2 | 0.2 | 0.2 |
| 4-(3-ethoxy-4-hydroxy-phenyl)butan-2-one | 0.5 | 0.5 | |
| 1,3-propanediol | 5 | 5 | |
| niacinamide | — | 3 | — |
| Water | qs 100 | qs 100 | qs 100 |
| Appearance at T0 | Two-phase with 2 clear and colorless phases | Two-phase with 2 clear and colorless phases | Two-phase with 2 clear and colorless phases |

The two-phase compositions according to the invention (examples 10 and 11) also exhibit conforming antimicrobial protection.

COMPARATIVE EXAMPLES 13 TO 15

The following 2 two-phase compositions according to the invention (examples 13 and 14) and a composition outside the invention (example 15) were prepared (contents by weight percentage) and the appearance of each composition obtained was observed.

| | Example 13 | Example 14 | Example 15* |
|---|---|---|---|
| Isopropyl palmitate | 4.5 | 4.5 | 4.5 |
| Isododecane | 4.5 | 4.5 | 4.5 |
| Isohexadecane | 6 | 6 | 6 |
| Decyl glucoside in aqueous solution at 55% by weight (ORAMIX NS 10 from SEPPIC) | 0.17 | 0.17 | 0.17 |
| Hexylene glycol | 0.4 | 0.4 | 0.4 |
| Sodium chloride | 0.4 | 0.4 | 0.4 |
| Potassium phosphate | 1 | 1 | 1 |
| Sequestrant | 0.2 | 0.2 | 0.2 |
| 4-(3-ethoxy-4-hydroxy-phenyl)butan-2-one | 0.5 | 0.5 | |
| 1,3-propanediol | 5 | 5 | |

|  | Example 13 | Example 14 | Example 15* |
| --- | --- | --- | --- |
| niacinamide | — | 3 | — |
| Water | qs 100 | qs 100 | qs 100 |
| Appearance at T0 | Two-phase with 2 clear and colorless phases | Two-phase with 2 clear and colorless phases | Two-phase with 2 clear and colorless phases |

The two-phase compositions according to the invention (examples 13 and 14) also exhibit conforming antimicrobial protection.

COMPARATIVE EXAMPLES 16 TO 18

The following 2 two-phase compositions according to the invention (examples 16 and 17) and a composition outside the invention (example 18) were prepared (contents by weight percentage) and the appearance of each composition obtained was observed.

|  | Example 16 | Exampl 17 | Example 18* |
| --- | --- | --- | --- |
| Isododecane | 9 | 9 | 9 |
| Isohexadecane | 6 | 6 | 6 |
| Decyl glucoside in aqueous solution at 55% by weight (ORAMIX NS 10 from SEPPIC) | 0.17 | 0.17 | 0.17 |
| Hexylene glycol | 0.4 | 0.4 | 0.4 |
| Sodium chloride | 0.4 | 0.4 | 0.4 |
| Monopotassium phosphate | 1 | 1 | 1 |
| Sequestrant | 0.2 | 0.2 | 0.2 |
| 4-(3-ethoxy-4-hydroxy-phenyl)butan-2-one | 0.5 | 0.5 | — |
| 1,3-propanediol | 5 | 5 | — |
| niacinamide | — | 3 | — |
| Water | qs 100 | qs 100 | qs 100 |
| Appearance at T0 | Two-phase with 2 clear and colorless phases | Two-phase with 2 clear and colorless phases | Two-phase with 2 clear and colorless phases |

The two-phase compositions according to the invention (examples 16 and 17) also exhibit conforming antimicrobial protection.

The invention claimed is:

1. A composition comprising an aqueous phase and an oily phase which are visually distinct and superimposed, 1,3-propanediol and a ketone compound of formula (I):

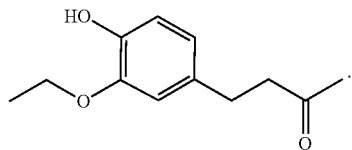

wherein:
RI represents a C2-C4 alkyl radical,
R2 represents a hydrogen atom, or a saturated or unsaturated, linear or branched, C1-C4 hydrocarbon-based radical;
R3 represents a saturated or unsaturated, linear or branched, C1-C4 hydrocarbon-based radical optionally substituted with a hydroxyl group;
C—X represents C=O; wherein the composition is not an emulsion.

2. The composition as claimed in claim 1, wherein for the compound (I):
R1 represents an ethyl radical;
R2 represents a hydrogen atom;
R3 represents a saturated or unsaturated, linear or branched, $C_1$-$C_4$ hydrocarbon-based radical optionally substituted with a hydroxyl group;
C—X represents C=O.

3. The composition as claimed in claim 1, wherein the compound (I) is:

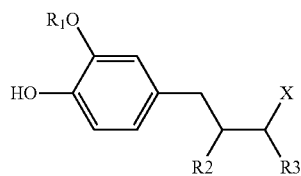

4. The composition as claimed in claim 3, wherein compound (I) is present in a content ranging from 0.01% to 5% by weight, relative to the total weight of the composition.

5. The composition as claimed in claim 3, wherein compound (I) is present in a content ranging from 0.01% to 3% by weight, relative to the total weight of the composition.

6. The composition as claimed in claim 3, wherein the 1,3-propanediol is present in a content ranging from 1 to 20% by weight.

7. The composition as claimed in claim 3, wherein the 1,3-propanediol is present in a content ranging from 2 to 10% by weight.

8. The composition as claimed claim 1, wherein the compound (I) is present in a content ranging from 0.01% to 5% by weight, relative to the total weight of the composition.

9. The composition as claimed in claim 8, wherein the 1,3-propanediol is present in a content ranging from 1 to 20% by weight.

10. The composition as claimed in claim 1, wherein the 1,3-propanediol is present in a content ranging from 0.1 to 50% by weight.

11. The composition as claimed in claim 1, wherein the aqueous phase is present in a content ranging from 25% to 95% by weight relative to the total weight of the composition.

12. The composition as claimed in claim 1, which comprises from 20% to 95% by weight of water, relative to the total weight of the composition.

13. The composition as claimed in claim 1, which further comprises a polyol that is water-miscible at ambient temperature (25° C.) having from 2 to 6 carbon atoms.

14. The composition as claimed in claim 13, wherein the water-miscible polyol is present in a content ranging from 0.1 to 40% by weight relative to the total weight of the composition.

15. The composition as claimed in claim 1, which comprises an electrolyte.

16. The composition as claimed in claim 1, wherein the weight ratio between the aqueous phase and the oily phase ranges from 10/90 to 90/10.

17. The composition as claimed in claim 1, wherein the oily phase comprises one or more oils chosen from mineral, plant or synthetic hydrocarbon-based oils, or alternatively silicone oils.

18. The composition as claimed in claim 1, which comprises a nonionic surfactant in an amount such that the aqueous and oily phase are distinct at rest and do not mix to form an emulsion.

19. The composition as claimed claim 1, which comprises an additive chosen from:
   (i) a niacinamide compound chosen from niacinamide, N,N-diethylniacinamide, N-picolylniacinamide and N-allylniacinamide;
   (ii) a xanthine compound of formula (II):

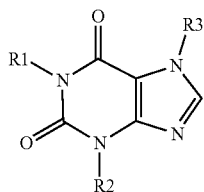

(II)

wherein:
R1, R2 and R3, independently of one another, denote a hydrogen atom or a methyl or ethyl radical;
the compound (I) may be xanthine (R1=R2=R3=H), caffeine (R1=R2=R3=methyl), theobromine (R1=H; R2=R3=methyl), theophylline (R1=R2=methyl; R3=H) and paraxanthine (R1=R3=methyl; R2=H); and mixtures thereof.

20. The composition as claimed claim 1, wherein the compound (I) is present in a content ranging from 0.01% to 5% by weight, relative to the total weight of the composition; the 1,3-propanediol is present in a content ranging from 1 to 20% by weight; the aqueous phase is present in a content ranging from 50% to 80% by weight relative to the total weight of the composition and which comprises from 45% to 80% by weight of water, relative to the total weight of the composition and wherein the compound (I) is:

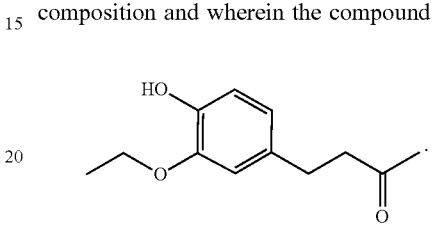

21. A process for the non-therapeutic cosmetic treatment of keratin materials, comprising the application to said keratin materials of a composition as claimed in claim 1.

* * * * *